United States Patent
Chenon et al.

(10) Patent No.: US 7,605,296 B2
(45) Date of Patent: Oct. 20, 2009

(54) METHOD FOR SEPARATING AND PURIFYING 2,6-DIMETHYLNAPHTHALENE

(75) Inventors: Yang-Ho Chenon, Gyeonggi-do (KR); Young-Gyo Choi, Gyeonggi-do (KR)

(73) Assignee: Hyosung Corporation, Seoul (KR)

( * ) Notice: Subject to any disclaimer, the term of this patent is extended or adjusted under 35 U.S.C. 154(b) by 387 days.

(21) Appl. No.: 11/595,514

(22) Filed: Nov. 8, 2006

(65) Prior Publication Data

US 2007/0255083 A1    Nov. 1, 2007

(30) Foreign Application Priority Data

May 1, 2006    (KR) .................. 10-2006-0039220

(51) Int. Cl.
C07C 7/14    (2006.01)
(52) U.S. Cl. .................. 585/812; 585/814; 585/816; 585/817
(58) Field of Classification Search .................. 585/812, 585/814, 816, 817
See application file for complete search history.

(56) References Cited

U.S. PATENT DOCUMENTS

| 4,992,619 | A | * | 2/1991 | Koide et al. .................. 585/817 |
| 5,220,098 | A | * | 6/1993 | Nakamura et al. .......... 585/812 |
| 5,675,022 | A |   | 10/1997 | Moyers et al. |

FOREIGN PATENT DOCUMENTS

| JP | 9-249586 | 9/1997 |
| JP | 9-301900 | 11/1997 |
| KR | 1996-0001908 | 2/1996 |
| KR | 2001-0033746 | 4/2001 |
| KR | 10-2003-0075336 | 9/2003 |

* cited by examiner

Primary Examiner—Tam M Nguyen
(74) Attorney, Agent, or Firm—Merchant & Gould P.C.

(57) ABSTRACT

A method for separating and purifying 2,6-dimethylnaphthalene, is provided in which 2,6-dimethylnaphthalene of high purity is obtained from a mixture of dimethylnaphthalene isomers with a high yield, by means of a combined process of column melt crystallization and sweating operation.

12 Claims, 4 Drawing Sheets

[FIG. 1]
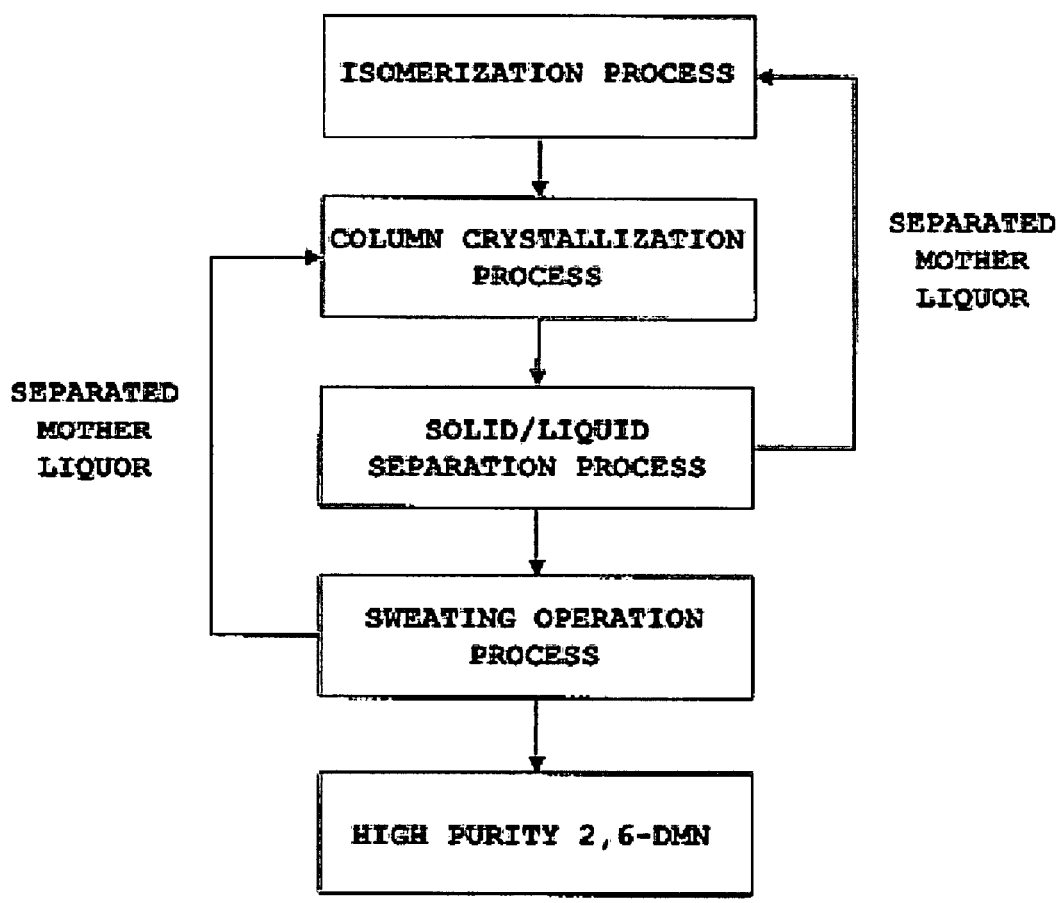

[FIG. 2]
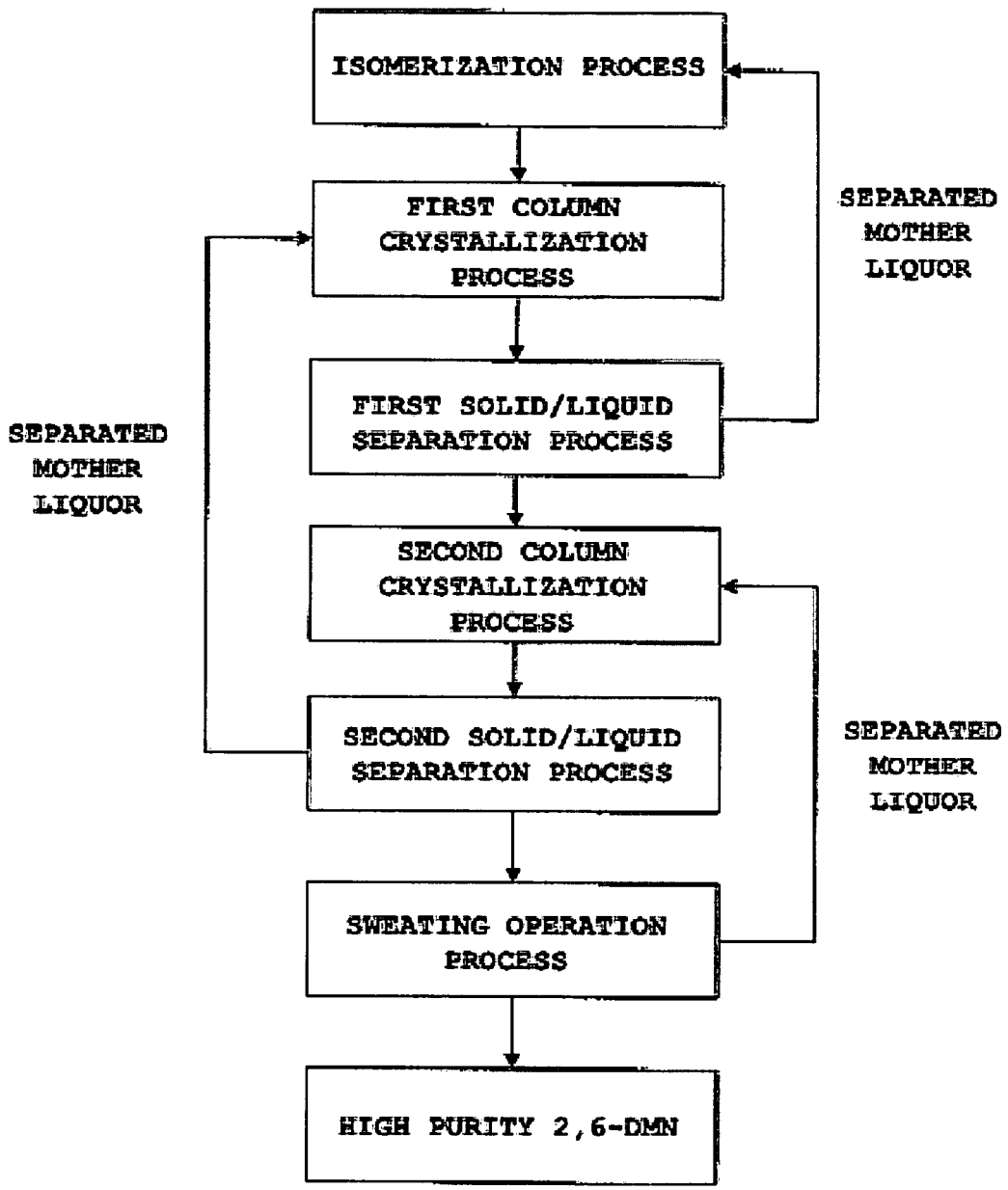

[FIG. 3]
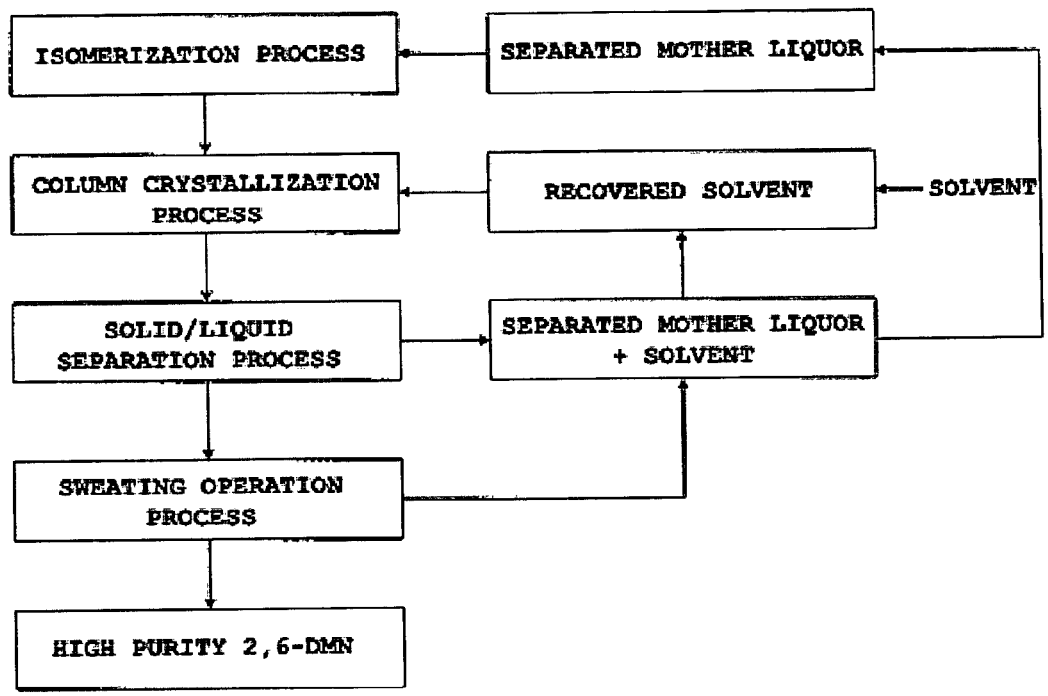

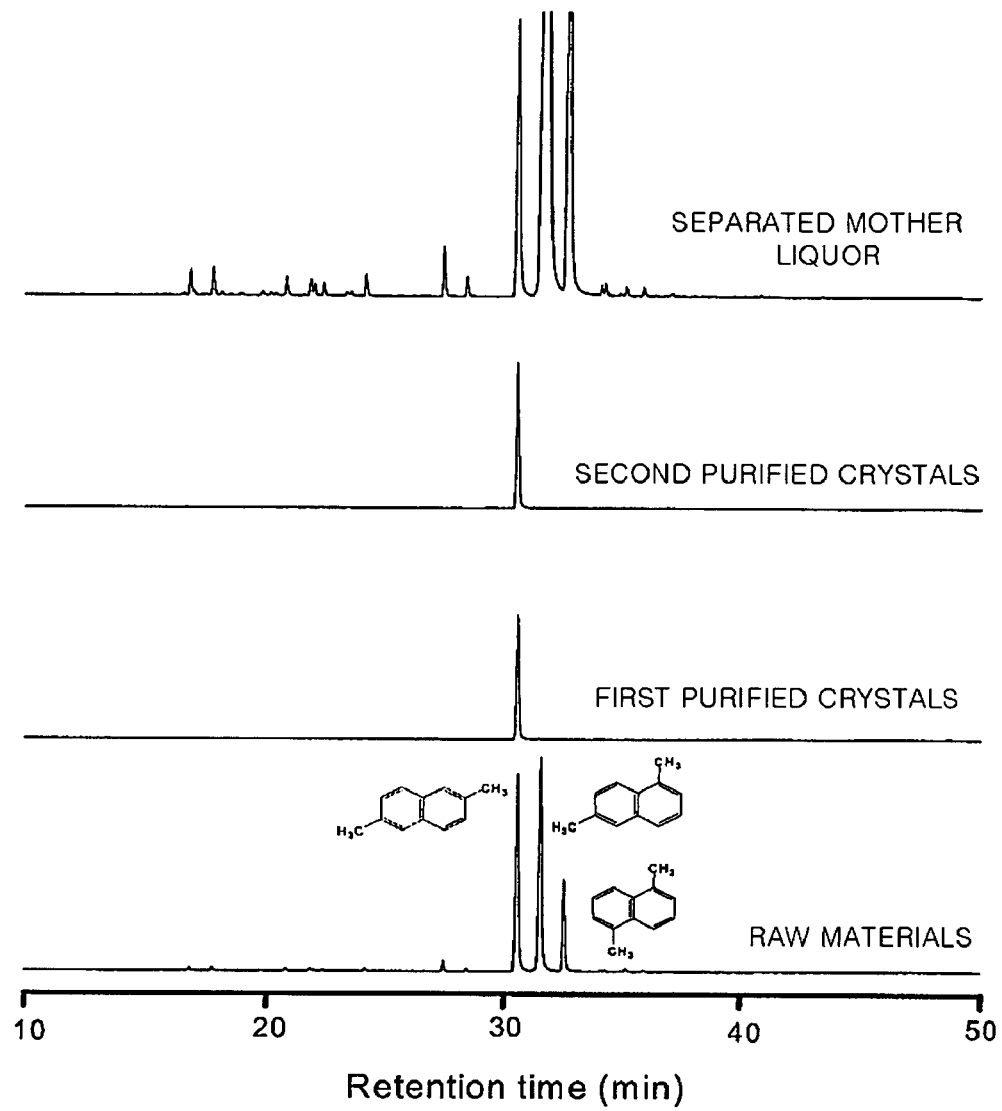
[FIG. 4]

METHOD FOR SEPARATING AND PURIFYING 2,6-DIMETHYLNAPHTHALENE

BACKGROUND OF THE INVENTION

1. Field of the Invention

The present invention relates to a method for separating and purifying 2,6-dimethylnaphthalene, and in particular, to a method for separating and purifying 2,6-dimethylnaphthalene, in which 2,6-dimethylnaphthalene of high purity is obtained from a mixture of dimethylnaphthalene isomers with a high yield, by means of a combined process of column melt crystallization and sweating operation.

2. Description of the Related Art 2,6-Dimethylnaphthalene (hereinafter, may be abbreviated to 2,6-DMN) is a raw material used for the production of fibers, films and the like made of polyethylenenaphthalate (PEN). Therefore, in order to produce a highly functional polyethylenenaphthalate, the raw material thereof, 2,6-dimethylnaphthalene, is also required to be a product of high purity.

In general, 2,6-dimethylnaphtahlene is produced by a series of reactions, starting from a reaction between o-xylene and butadiene followed by alkenation, cyclization, dehydrogenation and isomerization, and is finally obtained as an isomeric mixture rich in 2,6-dimethylnaphthalene. Dimethylnaphthalene (DMN) may exist in 10 different isomeric forms such as 2,6-DMN, 2,7-DMN, 2,3-DMN, 1,2-DMN, 1,3-DMN, 1,4-DMN, 1,5-DMN, 1,6-DMN, 1,7-DMN, and 1,8-DMN, depending on the positions of two methyl groups in the structure. Accordingly, in order to obtain 2,6-dimethylnaphthalene of high purity, a process of separating and purifying 2,6-dimethylnaphthalene from a mixture of dimethylnaphthalene isomers is required.

For the method for separating and purifying 2,6-dimethylnaphthalene widely used at present, such methods are known: 1) a method for separation by crystallization; 2) a method for separation by adsorption; 3) a method for forming a complex of 2,6-dimethylnaphthalene with a certain type of organic compound, separating this complex, and then decomposing the complex; and so on.

The techniques known in the related art, which are pertinent to the method for separating 2,6-dimethylnaphthalene, include the following.

Korean Patent No. 10-0463076 describes a method for separating 2,6-dimethylnaphthalene of high purity by selectively separating a mixture of dimethylnaphthalene isomers containing 2,6-dimethylnaphthalene from a naphthalenic mixture containing dimethylnaphthalene isomers through recrystallization, fractionation or the like, and then crystallizing 2,6-dimethylnaphthalene under pressure in the presence of a solvent. However, the dimethylnaphthalene isomers have very close boiling points, as shown in the following Table 1, and thus, it is difficult to separate and purify 2,6-dimethylnaphthalene by distillation.

TABLE 1

| DMN isomer | Melting point (° C.) | Boiling point (° C.) |
|---|---|---|
| 1,6-DMN | −16.0 | 266 |
| 1,7-DMN | −14.0 | 263 |
| 1,3-DMN | −4.2 | 265 |
| 1,2-DMN | −3.5 | 271 |
| 1,4-DMN | 6.0 | 265 |
| 1,8-DMN | 65.0 | 270 |
| 1,5-DMN | 82.0 | 269 |
| 2,7-DMN | 98.0 | 262 |
| 2,3-DMN | 104.0 | 269 |
| 2,6-DMN | 112.0 | 262 |

Furthermore, as shown in Table 1 above, the melting point of 2,6-dimethylnaphthalene is the highest among the isomers of 2,6-dimethylnaphthalene. Thus, it is possible to separate and purify 2,6-dimethylnaphthalene by melt crystallization.

Korean Laid-Open Patent Application No. 10-2001-33746 describes a method for producing 2,6-DMN of high purity with a high yield from a mixture of DMN isomers through a series of processes including fractionation, crystallization and adsorption, without restricting 2,6-DMN, which is to be used in the production of polyethylenenaphthalate, to a specific isomer present in the raw material supplied. The above method is characterized in that 2,6-DMN is dissolved in p-xylene and o-xylene as final purifying step through crystallization, to adsorb and separate it.

Japanese Laid-Open Patent Application No. 1997-249586 and Japanese Laid-Open Patent Application No. 1997-301900 describe methods for producing 2,6-DMN from a mixture of DMN isomers through crystallization in the presence of a solvent. These methods are directed to industrially advantageous means of separation and recovery, because the methods allow maintaining of the product purity at at least a predetermined level with stability over a long period of time.

U.S. Pat. No. 5,675,022 describes a method for dynamic melt crystallization using a Sulzer Chemtech apparatus, which is a falling film crystallizer, comprising flowing a molten liquid on a cooled surface, in the form of a liquid film, by means of forced convection. However, this method involves dynamic layer crystallization which disadvantageously requires performing crystallization 5 times or more through multi-stage (5-stage) crystallization, and use of additional apparatuses.

Korean Patent No. 10-0463076 describes a method for separation and purification to obtain 2,6-diemthylnaphthalene of high purity with a high yield, by separating 2,6-dimethylnaphthalene of high purity from residue oil of naphtha cracking and a mixture of dimethylnaphthalene isomers, through a combined process of melt crystallization and extractive crystallization. However, this method is operated in a batch mode, and thus has limitations in the throughput, and difficulties in scaling up, and the method is not suitable for the separation in an industrial scale.

Korean Patent No. 10-0100533 describes an industrially advantageous method for separating 2,6-dimethylnaphthalene of high purity from a feed material containing a mixture of dimethylnaphthalene isomers, by conducting separation by adsorption using an adsorbent comprising zeolite Y containing an alkali metal or zinc, and a desorbent containing 60% by weight or more of p-xylene or o-xylene.

Among these methods, the methods employing crystallization are known to be simplest and most suitable for industrial application. However, the methods employing crystallization have problems of requiring relatively high sums of fixed investment and production costs because the process is relatively complicated, results in a low yield, and makes use of expensive solvents. Particularly, in the case of using a separation process through crystallization, the separation process involves simple cooling and crystallization in most cases, and is focused on the process of isomerization or adsorption using catalyst, rather than crystallization.

BRIEF DESCRIPTION OF THE DRAWINGS

The above and other features and advantages of the present invention will become more apparent by describing in detail preferred embodiments thereof with reference to the attached drawings in which:

FIG. 1 is a process diagram schematically illustrating the method for separating and purifying 2,6-dimethylnaphthalene according to an embodiment of the present invention.

FIG. 2 is a process diagram schematically illustrating the method for separating and purifying 2,6-dimethylnaphthalene by performing the process of crystallization twice according to an embodiment of the present invention.

FIG. 3 is a process diagram schematically illustrating the method for separating and purifying 2,6-dimethylnaphthalene using a solvent in the crystallization process according to an embodiment of the present invention.

FIG. 4 is a graph showing the results of analyses by gas chromatography of the mixture of dimethylnaphthalene isomers used in the method of separation and purification, and of 2,6-dimethylnaphthalene obtained from the respective processes.

DESCRIPTION OF THE PREFERRED EMBODIMENTS

In this regard, the inventors of the present invention conducted researches on the method for separating and purifying 2,6-dimethylnaphthalene of high purity with a high yield from a mixture of dimethylnaphthalene isomers, and found that 2,6-dimethylnaphthalene of high purity can be obtained with a high yield from a mixture of dimethylnaphthalene isomers, by using a combined process of column melt crystallization using a column crystallization apparatus which induces the formation of crystal layers inside the column, and sweating operation of vacuum filtering the crystal layers and then partially melting the impurities contained on the surfaces of the formed crystal layers and between the crystal layers, thus completing the present invention.

Accordingly, an object of the present invention is to provide a method for separating and purifying 2,6-dimethylnaphthalene of high purity with a high yield from a mixture of dimethylnaphthalene isomers by means of a combined process of column melt crystallization and sweating operation.

Another object of the present invention is to provide a method for separating and purifying 2,6-dimethylnaphthalene, which method utilizes a simple apparatus and simplified operation, leading to reduced fixed investment and production costs.

The present invention provides a method for separating and purifying 2,6-dimethylnaphthalene, comprising the steps of:

1) performing melt crystallization to produce 2,6-dimethylnaphthalene using a column melt crystallization process for cooling a molten liquid of a mixture of dimethylnaphthalene (DMN) isomers;

2) separating the crystals produced in Step 1) from the mother liquor by vacuum suction filtration;

3) performing sweating operation to partially melt the impurities contained on the surfaces of the crystal layers formed in Step 2) and between the crystal layers, while suction filtering the impurities; and 4) melting the 2,6-dimethylnaphthalene crystals after the sweating operation, and separating and recovering 2,6-dimethylnaphthalene.

Hereinafter, the present invention will be described in detail.

FIG. 1 is a process diagram schematically illustrating the method for separating and purifying 2,6-dimethylnaphthalene by performing column melt crystallization and sweating operation once, according to an embodiment of the present invention.

The mixture of dimethylnaphthalene isomers used for the method for separating and purifying 2,6-dimethylnaphthalene according to the present invention, is a reaction mixture containing 2,6-dimethylnaphthalene, which is obtained from an isomerization reaction of dimethylnaphthalene. The reaction mixture containing 2,6-dimethylnaphthalene is a mixture containing 10 dimethylnaphthalene isomers (2,6-DMN, 2,7-DMN, 2,3-DMN, 1,2-DMN, 1,3-DMN, 1,4-DMN, 1,5-DMN, 1,6-DMN, 1,7-DMN, and 1,8-DMN), monomethylnaphthalene isomers (α-methylnaphthalene and β-methylnaphthalene), and low boiling point (220 to 270° C.) hydrocarbon compounds (e.g., biphenyls, alkanes, cycloalkanes, alkenes and cycloalkenes), in which 2,6-DMN, 1,5-DMN, 1,6-DMN and other compounds are contained in the respective contents indicated in the following Table 2.

TABLE 2

| Compound | Composition (wt %) | Boiling point (° C.) | Melting point (° C.) |
|---|---|---|---|
| 2,6-DMN | 20 to 80 | 262 | 112 |
| 1,5-DMN | 20 to 8 | 269 | 82 |
| 1,6-DMN | 25 to 6 | 266 | −16 |
| Others | 35 to 6 | — | — |

In the method for separating and purifying 2,6-dimethylnaphthalene according to the present invention, the first step is directed to a process of primary separation and purification by column melt crystallization, in which a mixture of DMN isomers containing 2,6-DMN of a purity of 75% by weight or greater is separated from the mixture of DMN isomers produced in the process for 2,6-DMN production.

The column melt crystallization method is performed in a column crystallization apparatus, in which the column crystallization apparatus comprises (i) a column crystallization vessel for forming crystal layers; (ii) an external crystallization vessel for storing the sample; (iii) a freezer equipped with a temperature controller for controlling the coolant temperature; (iv) a digital temperature recorder for recording the temperature profile; and (v) a gas chromatography system for analyzing the collected sample.

First, the mixture of DMN isomers is supplied to the column crystallization vessel, and the column crystallization vessel is maintained at a temperature 10° C. higher than the melting point of the mixture of DMN isomers, in order to maintain the reaction mixture comprising the mixture of DMN isomers in the molten state (melting point of 2,6-DMN=112° C., melting point of a mixture containing 45% by weight of 2,6-DMN=75±5° C.). Then, 2,6-DMN crystals are produced by lowering the temperature of the column crystallization vessel to a final cooling temperature of 0 to 65° C. in accordance with the composition of the raw material, at a cooling rate ranging from 0.1 to 1° C./min. Here, when the cooling temperature of the column crystallization vessel is 0° C. or lower, components other than 2,6-DMN are also converted to solid crystals, while when the cooling temperature is 65° C. or higher, no crystals are produced. Furthermore, when the cooling rate exceeds beyond the range described above, operation of the column crystallization vessel is difficult, and a large amount of impurities remain in the produced crystals due to the high rate of crystal growth caused by rapid cooling, thus deteriorating the product purity. The surface of the column crystallization vessel is cooled to 0 to 65° C. by means of a coolant formed by mixing water and ethylene glycol at a ratio of 3:1, and methanol, which are circulated in the internal jacket installed in the column crystallization vessel.

In the method for separating and purifying 2,6-dimethylnaphthalene according to the present invention, the second step is directed to a process of separating the crystals produced in the Step 1) from the mother liquor by vacuum suction filtration. The 2,6-DMN crystals thus produced by cooling are separated from the residual liquor (mother liquor remaining after crystallization) inside the column crystallization vessel. Here, the residual liquor is separated by vacuum suction filtration in a vacuum of 50 to 300 torr, and then sent to a mother liquor reservoir. The amount of crystals formed in the column crystallization vessel is determined from the amount of the residual liquor, and the compositions of the crystals and the residual liquor are analyzed by a gas chromatography system equipped with a flame ionization detector (FID). When the purity of 2,6-DMN reaches 75% by weight or greater, vacuum suction is stopped, and the third process of separation and purification by the sweating operation is carried out.

The purity and yield of the produced 2,6-DMN are calculated from the following Equation 1 and Equation 2.

Purity (%)=[(Weight of 2,6-*DMN* in the mixture)/ (Weight of the mixture in total)]×100  [Equation 1]

Yield (%)=[(Weight of 2,6-*DMN* obtained by crystallization or sweating operation)/(Weight of 2,6-*DMN* contained in the sample before crystallization)]×100  [Equation 2]

Meanwhile, in order to enhance the purity of crystals and to promote crystal growth during the column crystallization of 2,6-DMN, crystal seeds (2,6-DMN having a purity of 99% by weight or more) can be introduced. The temperature for crystal seed introduction is below the melting point of the mixture containing 2,6-DMN, that is, the crystal seeds are introduced at a temperature within the metastable region (the region between the saturation concentration and nucleation), and preferably at 65 to 75° C. Here, the amount of the crystal seeds to be introduced, when expressed as a weight ratio of the crystal seeds to the mixture of DMN isomers, is preferably 1/10000 to 1/100. If the amount of the crystal seeds to be introduced is less than or more than the range, the growth rate of the crystal layers is decreased, causing impurities to be included inside the crystals, and the purity is deteriorated.

The process of separation and purification by means of column melt crystallization is carried out once, or twice or more, and when the purity of 2,6-DMN reaches 75% by weight or greater, the process of separation and purification through the sweating operation is carried out. Twice-repeated crystallization means repeating the processes of separating the crystals obtained in the primary crystallization process from the residual liquor, and then sending the crystal products to the secondary crystallization process, while recirculating the mother liquor (See FIG. 2).

In the method for separating and purifying 2,6-dimethylnaphthalene according to the present invention, the third step is directed to a process of recovering 2,6-DMN by means of the sweating operation, in particular, a process of recovering 2,6-DMN having a purity of 99% by weight or more from the crystal product obtained in the previous crystallization process. Here, the temperature of the crystallization vessel is increased to 60 to 100° C. at a rate of 0.1 to 1° C./min, the crystals are subjected to vacuum suction filtration, and the remaining 2,6-DMN of high purity is melted and recovered. If the raised temperature is 100° C. or higher, the produced crystals melt again, thus causing a decrease in the yield, and the effect of the sweating operation cannot be maximized. If the raised temperature is 60° C. or lower, sweating does not occur. If the rate of temperature increase is less than or greater than the range, the yield is lowered.

It is also possible to separate and purify 2,6-dimethylnaphthalene by adding a certain amount of a solvent (ethanol) to the process of primary separation and purification by means of the column crystallization of the first step, and performing the processes of crystallization, sweating operation and solvent recovery in the same manner (See FIG. 3). When a solvent is used, the materials having higher solubility in the solvent can be easily removed, and thus, the separability can be enhanced. The ratio of solvents is preferably such that the mixture of DMN isomers:ethanol=1:0.5 to 1:5. If the ratio of solvents is less than or greater than the above-described range, 2,6-DMN of high purity can be obtained; however, the yield is lowered because of the relative solubility, and the isomeric mixture should be cooled to a very low temperature.

The results of analyses by gas chromatography of the mixture of DMN isomers used for the present invention, and of the respective products from the processes for separation and purification, are shown in FIG. 4. As such, the method for separating and purifying 2,6-dimethylnaphthalene according to the present invention allows separation of 2,6-DMN of high purity with a high yield from a mixture of DMN isomers containing 2,6-DMN, by means of a combined process of column melt crystallization and sweating operation.

Hereinafter, the present invention will be described in more detail with reference to preferred Examples. However, the following Examples are only for the illustrative purposes, and are not intended to limit the present invention by any means.

EXAMPLES 1 TO 6

Separation and Purification of Crystals with Varying Compositions of the Raw Material to be Introduced Separation and purification of the crystals according to the composition of the raw material to be introduced were performed by the method for separation and purification illustrated in FIG. 1.

70 kg each of mixtures of dimethylnaphthalene isomers (crude DMN) containing 22.71 to 46.23% by weight of 2,6-dimethylnaphthalene, was introduced into a 100-L column crystallization vessel equipped with a jacket, and a thermal medium was circulated in the jacket of the column crystallization vessel to maintain the temperature of the isomeric mixture at a temperature 10° C. higher than the melting point expected according to the composition for 30 minutes. Subsequently, the isomeric mixture was cooled to 0 to 45° C. at a cooling rate of 0.1° C./min, and the temperature was maintained at the final crystallization temperature for 30 minutes. The crystals thus produced were separated from the respective residual liquors, and the composition of the crystals was subjected to an analysis by gas chromatography. The purities of the respective obtained crystals at varying cooling rates during the crystallization process are presented in the following Table 3 (Examples 1 to 3) and Table 4 (Examples 4 to 6).

Next, the crystallization product obtained by separating the crystals from the residual liquor was maintained in the column crystallization vessel, and the sweating operation was performed by gradually raising the temperature of the jacket of the column crystallization vessel. The crystals obtained by raising the temperature to 55 to 70° C. at a heating rate of 0.1° C./min were subjected to an analysis by gas chromatography. The results of the separation and purification at varying cooling rates in the purification process (crystallization and sweating operation) are presented in the following Table 3 (Examples 1 to 3) and Table 4 (Examples 4 to 6).

TABLE 3

|  |  | Example 1 ||| Example 2 ||| Example 3 |||
| --- | --- | --- | --- | --- | --- | --- | --- | --- | --- | --- |
|  |  | Mixture of DMN isomers | Crystals obtained after crystallization | Crystals obtained after sweating operation | Mixture of DMN isomers | Crystals obtained after crystallization | Crystals obtained after sweating operation | Mixture of DMN isomers | Crystals obtained after crystallization | Crystals obtained after sweating operation |
| Component (wt %) | 2,6-DMN | 22.71 | 47.25 | 65.34 | 30.87 | 56.38 | 73.89 | 35.55 | 67.55 | 79.67 |
|  | 1,5-DMN | 20.09 | 33.95 | 27.00 | 13.97 | 29.19 | 15.62 | 8.39 | 24.06 | 15.14 |
|  | 1,6-DMN | 24.10 | 14.18 | 5.37 | 30.68 | 10.34 | 8.64 | 31.47 | 5.24 | 3.34 |
|  | Low boiling point material | 10.02 | 1.02 | 0.24 | 8.64 | 0.54 | 0.19 | 12.72 | 0.95 | 0.55 |
|  | High boiling point material | 14.44 | 2.13 | 1.38 | 5.66 | 1.03 | 0.71 | 7.92 | 1.53 | 0.92 |
|  | Other DMN isomers | 8.64 | 1.47 | 0.67 | 10.18 | 2.52 | 0.95 | 3.95 | 0.67 | 0.38 |
|  | Total | 100.0 | 100.0 | 100.0 | 100.0 | 100.0 | 100.0 | 100.0 | 100.0 | 100.0 |
| Yield (%) |  | 100.0 | 12.8 | 8.7 | 100.0 | 24.8 | 16.0 | 100.0 | 39.6 | 27.5 |
| Experimental conditions | Initial temp. of crystallization (° C.) |  | 70 |  |  | 80 |  |  | 90 |  |
|  | Final temp. of crystallization (° C.) |  | 0 |  |  | 25 |  |  | 45 |  |
|  | Cooling rate (° C./min) |  | 0.1 |  |  | 0.1 |  |  | 0.1 |  |
|  | Final temp. of sweating operation (° C.) |  | 55 |  |  | 65 |  |  | 65 |  |
|  | Heating rate (° C./min) |  | 0.1 |  |  | 0.1 |  |  | 0.1 |  |

TABLE 4

|  |  | Example 4 ||| Example 5 ||| Example 6 |||
| --- | --- | --- | --- | --- | --- | --- | --- | --- | --- | --- |
|  |  | Mixture of DMN isomers | Crystals obtained after crystallization | Crystals obtained after sweating operation | Mixture of DMN isomers | Crystals obtained after crystallization | Crystals obtained after sweating operation | Mixture of DMN isomers | Crystals obtained after crystallization | Crystals obtained after sweating operation |
| Component (wt %) | 2,6-DMN | 40.33 | 78.65 | 93.57 | 44.64 | 88.67 | 97.59 | 46.23 | 91.68 | 99.07 |
|  | 1,5-DMN | 6.36 | 2.13 | 1.02 | 5.47 | 1.29 | 0.54 | 6.14 | 1.00 | 0.36 |
|  | 1,6-DMN | 38.29 | 13.47 | 2.46 | 36.51 | 6.29 | 0.82 | 39.33 | 5.25 | 0.75 |
|  | Low boiling point material | 7.28 | 1.80 | 0.58 | 5.34 | 1.25 | 0.43 | 6.68 | 1.02 | 0.02 |
|  | High boiling point material | 2.41 | 1.69 | 0.68 | 1.55 | 0.95 | 0.30 | 0.48 | 0.35 | 0.16 |
|  | Other DMN isomers | 5.33 | 2.26 | 1.69 | 6.49 | 1.55 | 0.32 | 1.14 | 0.70 | 0.36 |
|  | Total | 100.0 | 100.0 | 100.0 | 100.0 | 100.0 | 100.0 | 100.0 | 100.0 | 100.0 |
| Yield (%) |  | 100.0 | 58.2 | 46.7 | 100.0 | 65.4 | 50.1 | 100.0 | 70.3 | 63.8 |
| Experimental conditions | Initial temp. of crystallization (° C.) |  | 90 |  |  | 90 |  |  | 90 |  |
|  | Final temp. of |  | 45 |  |  | 45 |  |  | 45 |  |

TABLE 4-continued

|  | Example 4 | | | Example 5 | | | Example 6 | | |
| --- | --- | --- | --- | --- | --- | --- | --- | --- | --- |
|  | Mixture of DMN isomers | Crystals obtained after crystallization | Crystals obtained after sweating operation | Mixture of DMN isomers | Crystals obtained after crystallization | Crystals obtained after sweating operation | Mixture of DMN isomers | Crystals obtained after crystallization | Crystals obtained after sweating operation |
| crystallization (° C.) | | | | | | | | | |
| Cooling rate (° C./min) | | 0.1 | | | 0.1 | | | 0.1 | |
| Final temp. of sweating operation (° C.) | | | 70 | | | 70 | | | 70 |
| Heating rate (° C./min) | | | 0.1 | | | 0.1 | | | 0.1 |

As shown in Table 3 and Table 4, the ability to separate and purify 2,6-DMN by the crystallization and the sweating operation, depending on the varying compositions of the raw materials to be introduced, was shown to be higher, as the purity of 2,6-DMN in the introduced composition was higher. That is, in Example 6, when the purity of the 2,6-DMN introduced was 46.23% by weight, the purity of the crystals obtained after the crystallization process was 91.68% by weight, and the yield was 70.3%, presenting a high yield and excellent separability. The purity of the crystals obtained after the process of sweating operation was 99.07% by weight, and the yield was 63.8%.

EXAMPLES 7 TO 12

Separation and Purification of Crystals at Varying Cooling Rates

In order to separate and purify 2,6-dimethylnaphthalene crystals from mixtures of dimethylnaphthalene isomers containing 41.71% by weight of 2,6-dimethylnaphthalene, at varying cooling rates (0.1 to 1° C./min), the separation and purification of crystals during the crystallization process were carried out in the same manner as in Example 1. The process of the sweating operation was also carried out in the same manner as in Example 1.

The results of the separation and purification at varying cooling rates are presented in the following Table 5.

As shown in Table 5, the ability to separate and purify 2,6-DMN by the crystallization and the sweating operation at varying cooling rates was such that as the cooling rate increased, the purity of 2,6-DMN and the yield were low.

EXAMPLES 13 TO 18

Separation and Purification of Crystals at Varying Crystallization Temperatures

In order to separate and purify 2,6-dimethylnaphthalene crystals from a mixture of dimethylnaphthalene isomers containing 43.25% by weight of 2,6-dimethylnaphthalene at varying crystallization temperatures (final crystallization temperature: 65, 55 and 45° C.), the separation and purification of crystals were carried out in the same manner as in Example 1. The process of sweating operation was also carried out in the same manner as in Example 1.

The results of separation and purification at varying crystallization temperatures are presented in the following Table 6.

TABLE 5

|  | Mixture of DMN isomers (Feed) | Crystals obtained after crystallization | | | Crystals obtained after sweating operation | | |
| --- | --- | --- | --- | --- | --- | --- | --- |
|  |  | Ex. 7 Cooling rate 0.1° C./min | Ex. 8 Cooling rate 0.3° C./min | Ex. 9 Cooling rate 1° C./min | Ex. 10 Cooling rate 0.1° C./min | Ex. 11 Cooling rate 0.3° C./min | Ex. 12 Cooling rate 1° C./min |
| Purity of 2,6-DMN (%) | 41.71 | 90.72 | 78.16 | 73.51 | 99.32 | 98.71 | 97.08 |
| Yield (%) | 100.0 | 66.7 | 57.8 | 40.3 | 49.6 | 45.2 | 31.2 |

TABLE 6

|  | Mixture of DMN isomers (Feed) | Crystals obtained after crystallization | | | Crystals obtained after sweating operation | | |
| --- | --- | --- | --- | --- | --- | --- | --- |
|  |  | Ex. 13 Crystallization temp. 65° C. | Ex. 14 Crystallization temp. 55° C. | Ex. 15 Crystallization temp. 45° C. | Ex. 16 Crystallization temp. 65° C. | Ex. 17 Crystallization temp. 55° C. | Ex. 18 Crystallization temp. 45° C. |
| Purity of 2,6-DMN (%) | 43.25 | 95.70 | 91.36 | 90.72 | 99.52 | 99.37 | 99.15 |
| Yield (%) | 100.0 | 40.6 | 58.9 | 65.2 | 25.7 | 40.3 | 49.61 |

As shown in Table 6, the ability to separate and purify 2,6-DMN by the crystallization and the sweating operation at varying crystallization temperatures was such that, as the crystallization temperature was higher, the purity of 2,6-DMN was higher, while the yield was lower.

EXAMPLES 19 TO 21

Separation and Purification of Crystals at Varying Heating Rates During Sweating Operation In order to examine the extent of separation and purification of 2,6-dimethylnaphthalene from a mixture of dimethylnaphthalene isomers containing 39.75% to 41.06% by weight of 2,6-dimethylnaphthalene at varying heating rates (0.1 to 1° C./min) during the sweating operation, the separation and purification of crystals were carried out in the same manner as in Example 1.

The results of the separation and purification at varying heating rates during the sweating operation are presented in the following Table 7.

EXAMPLES 22 TO 25

Separation and Purification of Crystals at Varying Amounts of Crystal Seeds Introduced In order to examine the effect of the amount of crystal seeds introduced on the separation by crystallization, the process of column melt crystallization was carried out in the same manner as in Example 1.

70 kg each of mixtures of dimethylnaphthalene isomers containing about 39.57 to 41.04% by weight of 2,6-dimethylnaphthalene was introduced into a column crystallization vessel equipped with a jacket, and a thermal medium was circulated in the jacket of the column crystallization vessel to maintain the temperature at 85° C. for 30 minutes. Subsequently, the mixture was cooled to 45° C. at a cooling rate of 0.1° C./min, and the temperature was maintained at 45° C. for 30 minutes. In order to examine the effect of the amount of crystal seeds introduced, the crystallization process was carried out without any crystal seeds introduced, and while varying the amount of the crystal seeds introduced to 0.007, 0.07 and 0.7 kg, respectively. The crystals thus produced were separated from the respective residual liquors, and the respective compositions of the crystals were subjected to an analysis by gas chromatography. The results are presented in the following Table 8.

TABLE 7

|  | Example 19 Heating rate = 0.1° C./min | | | Example 20 Heating rate = 0.5° C./min | | | Example 21 Heating rate = 1° C./min | | |
| --- | --- | --- | --- | --- | --- | --- | --- | --- | --- |
|  | Mixture of DMN isomers (Feed) | Crystals obtained after crystallization | Crystals obtained after sweating operation | Mixture of DMN isomers (Feed) | Crystals obtained after crystallization | Crystals obtained after sweating operation | Mixture of DMN isomers (Feed) | Crystals obtained after crystallization | Crystals obtained after sweating operation |
| Purity of 2,6-DMN (%) | 41.06 | 90.91 | 99.03 | 39.75 | 89.90 | 99.03 | 40.53 | 90.33 | 98.75 |
| Yield (%) | 100.0 | 65.7 | 46.4 | 100.0 | 64.3 | 38.5 | 100.0 | 65.2 | 29.3 |

As shown in Table 7, the ability to separate and purify 2,6-DMN by the sweating operation according to the heating rate was such that, as the heating rate was higher, the purity of 2,6-DMN was higher, while the yield was lower.

TABLE 8

Crystallization - effect of amount of crystal seeds introduced

| | Example 22 Without crystal seeds | | Example 23 Amount of crystal seeds 0.007 kg | | Example 24 Amount of crystal seeds 0.07 kg | | Example 25 Amount of crystal seeds 0.7 kg | |
|---|---|---|---|---|---|---|---|---|
| | Mixture of DMN isomers (Feed) | Crystals obtained after crystalization | Mixture of DMN isomers (Feed) | Crystals obtained after crystalization | Mixture of DMN isomers (Feed) | Crystals obtained after crystalization | Mixture of DMN isomers (Feed) | Crystals obtained after crystalization |
| Purity (%) | 39.57 | 89.8 | 41.04 | 91.2 | 39.95 | 89.65 | 40.62 | 87.53 |
| Yield (%) | 100.0 | 65.3 | 100.0 | 67.2 | 100.0 | 67.9 | 100.0 | 70.2 |

As shown in Table 8, the ability to separate and purify 2,6-DMN with varying amounts of crystal seeds introduced in the crystallization process was such that, when the amount of the crystal seeds introduced, expressed as a weight ratio of the crystal seeds to the mixture of dimethylnaphthalene isomers introduced, was 1/10000 to 1/100, the purity and yield of 2,6-dimethylnaphthalene were higher compared with the case where no crystal seeds were introduced.

EXAMPLE 26

Separation and Purification of Crystals by Column Melt Crystallization Process Repeated Twice The process of separation and purification illustrated in FIG. 2 was carried out. The reason for carrying out the process of separation and purification of FIG. 2 was to investigate the possibility of performing the separation and purification for a shortened time by solving the problem due to the low cooling rate of the single-time crystallization process.

This is carried out by performing a primary crystallization process followed by a secondary crystallization process, and then performing the sweating operation. 70 kg of a mixture of dimethylnaphthalene isomers containing 42.78% by weight of 2,6-dimethylnaphthalene was introduced into a primary column crystallization vessel equipped with a jacket, and a thermal medium was circulated in the jacket of the column crystallization vessel to maintain the temperature at 85° C. for 30 minutes and to melt the isomeric mixture. Subsequently, the isomeric mixture was cooled to 45° C. at a cooling rate of 0.3° C./min, and the temperature was maintained at 45° C. for 30 minutes. The crystals thus produced were separated from the respective residual liquor, and the composition of the crystals was subjected to an analysis by gas chromatography. The results are presented in the following Table 9.

In addition, the crystals obtained from the primary crystallization process were sent, in the molten state, to a secondary crystallization vessel, and the secondary crystallization process was carried out in the same manner as in the primary crystallization process. During the secondary crystallization process, the temperature was maintained at 100° C. for 30 minutes to melt the crystals, and then the crystals were cooled to 60° C. at a cooling rate of 0.3° C./min, and were maintained at 60° C. for 30 minutes. The crystals thus produced were separated from the mother liquor, and were subjected to the sweating operation. The sweating operation was carried out, while increasing the temperature from 60° C. to 95° C. at a heating rate of 0.1° C./min.

TABLE 9

| | Mixture of DMN isomers | Primary crystallization | Secondary crystallization | Sweating operation |
|---|---|---|---|---|
| Purity (%) | 42.78 | 75.91 | 89.20 | 99.90 |
| Yield at each step (%) | 100.0 | 56.9 | 75.6 | 39.3 |
| Total yield (%) | 100.0 | 56.9 | 45.2 | 35.8 |

As shown in Table 9, the process illustrated in FIG. 2 was carried out (without recirculation), and as a result, a purity of 99.9% or more and a yield of 35% or more could be obtained. When a process of recirculating the residual liquor is employed as shown in FIG. 2, a purity of 99.9% or more and a yield of 80% or more can be obtained.

EXAMPLES 27 TO 32

Crystallization with Ethanol Solvent Added

The process of separation and purification illustrated in FIG. 3 was carried out.

50 to 10 kg each of mixtures of dimethylnaphthalene isomers containing 41.11% by weight or 41.36% by weight of 2,6-dimethylnaphthalene was mixed with 10 to 50 kg of ethanol as a solvent, were introduced in to a column crystallization vessel equipped with a jacket, and a thermal medium was circulated in the jacket to maintain the temperature of the isomeric mixture at 80° C. for 10 minutes to melt the isomeric mixture. Then, the isomeric mixture was cooled to 0° C. at a cooling rate of 0.1° C./min and maintained at 0° C. for 30 minutes. The crystals thus obtained were separated from the residual liquor by suction filtration. The respective crystal products obtained were subjected to an analysis by gas chromatography, and the results are presented in the following Table 10 (Examples 27 to 29) and Table 11 (Examples 30 to 32).

In addition, the crystals of the respective Examples above were subjected to the sweating operation by gradually increasing the temperature in the same manner as in Example 1. The temperature was raised up to 65° C. at a heating rate of 0.1° C./min, and the obtained results are presented in the following Table 10 and Table 11.

TABLE 10

| | Example 27 DMN:ethanol = 5:1 | | | Example 28 DMN:ethanol = 3:1 | | | Example 29 DMN:ethanol = 1:1 | | |
|---|---|---|---|---|---|---|---|---|---|
| | Mixture of DMN isomers (Feed) | Crystals obtained after crystallization | Crystals obtained after sweating operation | Mixture of DMN isomers (Feed) | Crystals obtained after crystallization | Crystals obtained after sweating operation | Mixture of DMN isomers (Feed) | Crystals obtained after crystallization | Crystals obtained after sweating operation |
| Purity of 2,6-DMN (%) | 41.11 | 90.54 | 99.08 | 39.61 | 91.54 | 99.35 | 40.82 | 93.31 | 99.54 |
| Yield (%) | 100.0 | 60.2 | 43.4 | 100.0 | 54.3 | 38.1 | 100.0 | 45.2 | 30.7 |

TABLE 11

| | Example 30 DMN:ethanol = 1:3 | | | Example 31 DMN:ethanol = 1:5 | | | Example 32 DMN:ethanol = 1:10 | | |
|---|---|---|---|---|---|---|---|---|---|
| | Mixture of DMN isomers (Feed) | Crystals obtained after crystallization | Crystals obtained after sweating operation | Mixture of DMN isomers (Feed) | Crystals obtained after crystallization | Crystals obtained after sweating operation | Mixture of DMN isomers (Feed) | Crystals obtained after crystallization | Crystals obtained after sweating operation |
| Purity of 2,6-DMN (%) | 41.36 | 93.97 | 99.75 | 39.19 | 95.18 | 99.68 | 40.89 | 95.33 | 99.91 |
| Yield (%) | 100.0 | 38.7 | 26.4 | 100.0 | 30.3 | 18.5 | 100.0 | 25.2 | 10.3 |

As shown in Table 10 and Table 11, in the process of separation and purification of primary crystallization using a column crystallization vessel, the purity was increased as the content of the solvent ethanol increased, but the relative yield of the crystals obtained was decreased. This is attributable to the difference in solubility, and it can be seen that, when the conditions for the crystallization operation such as the cooling temperature, the cooling rate, the heating rate and the like are controlled, superior results are obtained, as compared with the case of not using a solvent.

The method for separating and purifying 2,6-dimethylnaphthalene according to the present invention allows obtaining of 2,6-dimethylnaphthalene of high purity with a high yield from a mixture of dimethylnaphthalene isomers by means of a combined process of column melt crystallization and sweating operation. Further, the method for separating and purifying 2,6-dimethylnaphthalene according to the present invention involves a simpler process compared with conventional processes because the process is carried out by simple solid-liquid separations, and is an energy-saving process since the process uses the heat of melting, which is about one-fifth of the heat of vaporization used in distillation operations. In addition, the separation and purification apparatus is simple in structure, with operation thereof being also simple, and thus, the fixed investment and production costs can be reduced. The method is also suitable for industrial application since scaling up is possible, and thus is economically advantageous.

What is claimed is:

1. A method for separating and purifying 2,6-dimethylnaphthalene, comprising the steps of:
   1) performing melt crystallization to produce 2,6-dimethylnaphthalene crystals using a column melt crystallization process of adding a mixture of dimethylnaphthalene (DMN) isomers containing 2,6-dimethylnaphthalene to a column crystallization apparatus, melting the mixture in the apparatus, and then cooling a molten liquid of the mixture;
   2) forming 2,6-dimethylnaphthalene crystal layers by separating the 2,6-dimethylnaphthalene crystals produced in Step 1) from the mother liquor by vacuum suction filtration;
   3) performing a sweating operation of partially melting the impurities contained on the surfaces of the 2,6-dimethylnaphthalene crystal layers formed in Step 2) and between the 2,6-dimethylnaphthalene crystal layers, while suction filtering the impurities; and
   4) melting the 2,6-dimethylnaphthalene crystals after the sweating operation, and separating and recovering 2,6-dimethylnaphthalene.

2. The method for separating and purifying 2,6-dimethylnaphthalene as set forth in claim 1, wherein the cooling temperature in the column melt crystallization process of Step 1) is in the range of 0 to 65° C. in accordance with the composition of the raw material.

3. The method for separating and purifying 2,6-dimethylnaphthalene as set forth in claim 1, wherein the cooling rate in the column melt crystallization process of Step 1) is in the range of 0.1 to 1° C./min.

4. The method for separating and purifying 2,6-dimethylnaphthalene as set forth in claim 1, wherein the vacuum suction in Step 2) is performed by vacuum suction filtration at 50 to 300 torr.

5. The method for separating and purifying 2,6-dimethylnaphthalene as set forth in claim 1, wherein the heating rate in the sweating operation of Step 3) is in the range of 0.1 to 1° C./min.

6. The method for separating and purifying 2,6-dimethylnaphthalene as set forth in claim 1, wherein the heating temperature in the sweating operation of Step 3) is in the range of 60 to 100° C.

7. The method for separating and purifying 2,6-dimethylnaphthalene as set forth in claim 1, wherein the mixture of dimethylnaphthalene isomers contains 20 to 80% by weight of 2,6-dimethylnaphthalene.

8. The method for separating and purifying 2,6-dimethylnaphthalene as as set forth in claim 1, wherein crystal seeds are introduced in Step 1).

9. The method for separating and purifying of 2,6-dimethylnaphthalene as set forth in claim 8, wherein the amount of the crystal seeds to be introduced is such that the weight ratio of the crystal seeds/the mixture of dimethylnaphthalene isomers is 1/10000 to 1/100.

10. The method for separating and purifying 2,6-dimethylnaphthalene as set forth in claim 1, wherein ethanol is added in Step 1) as a solvent.

11. The method for separating and purifying 2,6-dimethylnaphthalene as set forth in claim 10, wherein the ratio of solvents is such that the mixture of dimethylnaphthalene isomers:ethanol=1:0.5 to 1:5.

12. The method for separating and purifying 2,6-dimethylnaphthalene as set forth in claim 1, wherein the Steps 1) and 2) are repeated twice or more.

\* \* \* \* \*